(12) United States Patent
Sun et al.

(10) Patent No.: US 7,425,667 B2
(45) Date of Patent: Sep. 16, 2008

(54) METHODS TO PRODUCE DESIRED PROTEINS IN PLANTS

(75) Inventors: Samuel Sai Ming Sun, Shatin (CN); Qiao Quan Liu, Jiangsu (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 11/254,401

(22) Filed: Oct. 20, 2005

(65) Prior Publication Data

US 2007/0083944 A1   Apr. 12, 2007

Related U.S. Application Data

(60) Provisional application No. 60/726,001, filed on Oct. 11, 2005.

(51) Int. Cl.
  *A01H 1/00*   (2006.01)
  *C07H 21/04*  (2006.01)
  *C07K 14/415* (2006.01)
  *C12N 15/29*  (2006.01)

(52) U.S. Cl. .................. 800/295; 435/6; 435/69.1; 435/468; 435/419; 435/252.3; 435/320.1; 530/370; 536/23.6; 800/278

(58) Field of Classification Search .............. None
See application file for complete search history.

(56) References Cited

U.S. PATENT DOCUMENTS 6,184,437 B1   2/2001  Sun et al.
6,753,167 B2 *  6/2004  Moloney et al. ........... 435/69.8
6,762,345 B1 *  7/2004  Cahoon et al. ............. 800/281

OTHER PUBLICATIONS

Prat et al. Nucleic Acids Research, Mar. 11, 1985, vol. 13, No. 5, pp. 1493-1504.*
La Vallie et al., Current Opinion in Biotech (1995) 6:501-506.
Mertz et al., Science (1964) 145:279-280.
Parmenter et al., Plant Mol. Biol. (1995) 29:1167-1180.
Sardana et al., Transgenic Res. (2002) 11:521-531.
Sun et al., In Vitro Cell. Dev. Biol.-Plant (2004) 40:155-162.
Sun et al., "Transgenic plants for improving seed storage proteins" in Transgenic Plants, vol. 1, S.D. Kung and R. Wu. (Eds.), Academic Press (1992) pp. 339-372.
Van Rooijen et al., Bio/Technology (1995) 13:72-77.
Vendekerckhove et al., Bio/Technology (1989) 7:929-932.

* cited by examiner

*Primary Examiner*—Phuong T Bui
(74) *Attorney, Agent, or Firm*—Morrison & Foerster LLP

(57) ABSTRACT

Fusion proteins that comprise at least one subunit of glutelin and a desired protein permit enhanced production of the desired protein in a useable form in plants. Such fusion proteins may be used to improve the nutritional value of plants, such as rice, by enhancing the production of specific essential amino acids in a useable form.

9 Claims, 2 Drawing Sheets

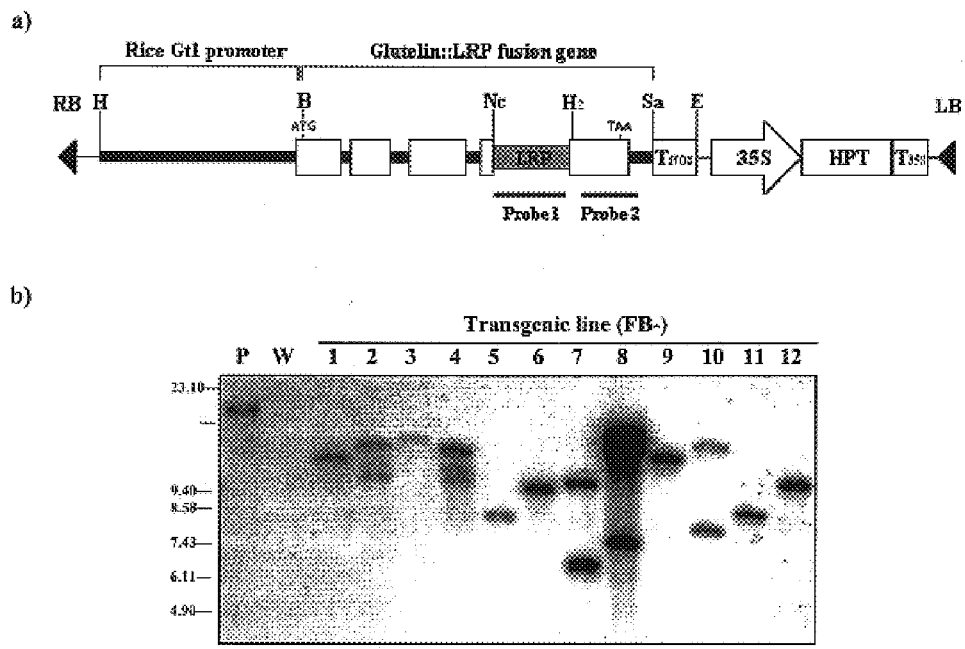
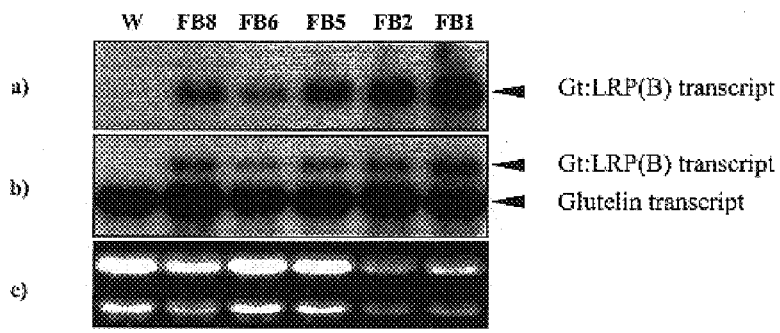
Figure 1
Figure 2

METHODS TO PRODUCE DESIRED PROTEINS IN PLANTS

CROSS-REFERENCE TO RELATED APPLICATIONS

This application claims benefit under 35 U.S.C. § 119(e) to provisional application filed 11 Oct. 2005, serial number not yet assigned, bearing the same title, and incorporated herein by reference.

TECHNICAL FIELD

The present invention relates to plant gene expression systems for useful proteins. Such proteins include pharmaceuticals, antibody chains, and proteins of high nutritional value. The invention resides in producing a desired protein as a fusion with the plant storage protein glutelin. The fusion protein may be produced in seeds using seed-specific promoters or in other portions of the plant, depending on the selection of control sequences.

BACKGROUND ART

It has long been known that it may be advantageous to produce desired proteins as fusions, especially with amino acid sequences homologous to the expression host. For example, LaVallie, E. R., et al., *Current Opinion in Biotech* (1995) 6:501-506 provides a summary and review of the use of expression of fusions of desired proteins in *E. coli* to overcome the problems associated with bacterial expression, such as the formation of inclusion bodies (which require refolding schemes) or failure of *E. coli* completely to remove the amino terminal methionine initiation codon. Fusion proteins have also been employed in plants with mixed results. For example, Parmenter, D. L., et al., *Plant Mol. Biol.* (1995) 29:1167-1180 describe the production of the anticoagulant protein, hirudin, as a fusion with the seed-specific protein, oleosin. Oleosins are small proteins and are imbedded in the phospholipid monolayer of oil bodies, and thus the fusions are relatively easy to purify. Successful production of hirudin in rape seed was achieved using this strategy. Successful fusion of the oleosin coding sequence with the heterologous β-glucuronidase in *Brassica napus* seeds was also demonstrated by Van Rooijen, G. J. H., et al., *Bio/technology* (1995) 13:72-77. On the other hand, while Vendekerckhove, J., et al., *Bio/technology* (1989) 7:929-932 produced the foreign protein Leu-enkephalin in *B. napus* and *Arabidopsis* seeds using a fusion with the 2S seed storage albumin protein, it appears that this was less successful due to the impact of the fusion on the post-translational fate of the modified seed storage protein.

Particularly relevant is the report by Sardana, R. K., et al., *Transgenic Res.* (2002) 11:521-531 which reports the production of human granulocyte-macrophage colony stimulating factor (GM-CSF) in transgenic tobacco plants under the control of the rice endosperm-specific glutelin promoter Gt3 to produce a fusion with the eight N-terminal amino acids of glutelin. It appeared that protein extracts from plants with either the construct comprising the eight glutelin amino acids or GM-CSF alone were biologically active.

While the present invention relates to fusions for production of desired proteins in general in plants, a particular application is the use of such fusion proteins to improve nutritional content. Plant proteins are relatively low in the nine essential amino acids required by mammalian consumers. Thus, for example, the nutritional value of cereal grain proteins is a critical constraint in their uses for both human food and animal feed, as they are mostly deficient in lysine and other essential amino acids (Sun, S. S. M., et al., *Transgenic Plants* (1993) 1:339-371). Rice, a low cost energy and protein source and the staple food of over half of the world's population, is relatively unbalanced in essential amino acid content, with lysine being the first limiting essential amino acid. It is costly and sometimes not feasible to supplement the cereal seeds with crystalline lysine or other nutritionally balanced proteins to correct for the deficiency. Therefore, improvement of rice seed proteins for increased lysine content is of extreme importance for those who rely upon rice as main staple food.

Significant effort has been made in the past to improve the quality (lysine content) of cereal grain proteins, e.g., maize opaque-2 (o2) mutant (Mertz, E. T., et al., *Science* (1964) 145:279-280). Unfortunately, undesirable traits often associated with such modified crops, such as lower yields and greater susceptibility to pests and diseases, preventing their agronomic utilization. Similarly, efforts in breeding rice containing increased lysine have not met with significant success. Recently with progress in biotechnology, enhancement of the nutritional value of crops has been shown to be feasible by introducing heterologous or modified genes encoding storage proteins rich in essential amino acids. For example, the contents of sulfur-containing amino acids, methionine and cysteine, but not of lysine, have been enhanced in legume and other crops, especially in cereal crops (Sun, S. S. M., et al., *In Vitro Cell. Dev. Biol.-Plant* (2004) 40:155-162).

Cloning of cDNA encoding a 18-kDa lysine-rich protein (LRP) from winged bean (*Psophocarpus tetragonolobus*) is disclosed in Sun, S. S. M., et al., U.S. Pat. No. 6,184,437. With a 10.7 mol % lysine content, this protein has great potential for improving the content of lysine in cereal crops. More recently, LRP has demonstrated to be tissue-specifically expressed in the seeds of transgenic rice plants under the control of the rice glutelin Gt1 promoter, and stably accumulated in the mature seeds of transgenic rice (Liu, et al., unpublished). The accumulation level of LRP in transgenic rice seeds was not particularly high, however, amounting only to about 1% of the total seed storage protein even in the highest expression lines, resulting in only a few % increase in lysine content in the dry rice seeds. Therefore, further lysine enhancement is required for effective improvement of the nutritional value of cereal grains.

Even if use of heterologous proteins could be achieved by enhancement at transcriptional level, as by strong seed-specific promoters, barriers still exist with regard to the various posttranscriptional steps required to produce a stable mature protein, such as, for example, conformation and subcellular targeting and deposition. In previous studies, we had attempted to enhance the expression of LRP gene by using a stronger promoter and/or fusing with signal peptide sequences of rice storage protein genes, but did not observe significant increase in the yield of protein in the mature transgenic rice seeds (Liu, et al., unpublished).

DISCLOSURE OF THE INVENTION

The present invention takes advantage of the highly efficient synthesis and packaging system of the seed storage protein glutelin to permit production of fusion proteins comprising the amino acid sequence of at least one glutelin subunit and a desired protein sequence. Among proteins that may be produced are those that add to the nutritional value of plants. In one embodiment, the lysine content is improved.

In one aspect, therefore, the invention is directed to fusion proteins comprising the amino acid sequence of a desired protein fused to the amino acid sequence of at least one subunit of a glutelin. A linker sequence optionally containing a cleavage site, in particular, an enzymatic cleavage site, may also be included. The desired protein may have enhanced nutritional value and/or may exhibit other desirable properties. The invention also includes recombinant materials for the production of these proteins, including expression systems, vectors comprising said expression systems, plant cells and plants containing these expression systems and the resulting fusion protein, and various plant parts, in particular, seeds which contain them and/or the fusion proteins themselves. The glutelin may be of any plant origin.

The invention is illustrated by modifying the rice native Gt1 gene encoding glutelin storage protein by fusing with a heterologous cDNA encoding a lysine-rich protein (LRP) from winged bean (*P. tetragonolobus*) to form a Gt:LRP fusion protein gene that can be highly expressed for nutrition improvement; however, other glutelin genes may also be used, and other proteins besides LRP may be produced as fusions. As the glutelin protein has two subunits, the desired protein sequence may be coupled to one or the other or both. The fusions may further include linker moieties, optionally containing cleavage sites to permit recovery of the desired protein independent of the glutelin sequence.

Thus, the invention also includes DNA constructs for the invention fusion proteins under the control of a promoter sequence that confers seed-specific expression. Either monocots or dicots are modified to contain the construct. Rice (*Oryza sativa* L.), a nutritionally incomplete staple food due to its deficiency in essential amino acid lysine, is used only to illustrate the invention.

Also included within the scope of the invention are methods to modify plants to contain the DNA constructs of the invention, food and food supplements generated from the resulting plants or progeny or parts thereof, and methods to enhance nutrition by using these foodstuffs.

BRIEF DESCRIPTION OF THE DRAWINGS

FIG. 1*a* shows a diagram of the binary construct pGLF-B for rice transformation. FIG. 1*b* is a Southern blot analysis of transgenic rice plants. The LRP and Gt1 specific probes used for both Southern and Northern blot analysis are indicated by "Probe 1" and "Probe 2," respectively.

FIGS. 2*a*-2*c* show Northern blot analysis of the expression of the Gt:LRP(B) fusion protein gene in transgenic rice.

MODES OF CARRYING OUT THE INVENTION

Figure 3:
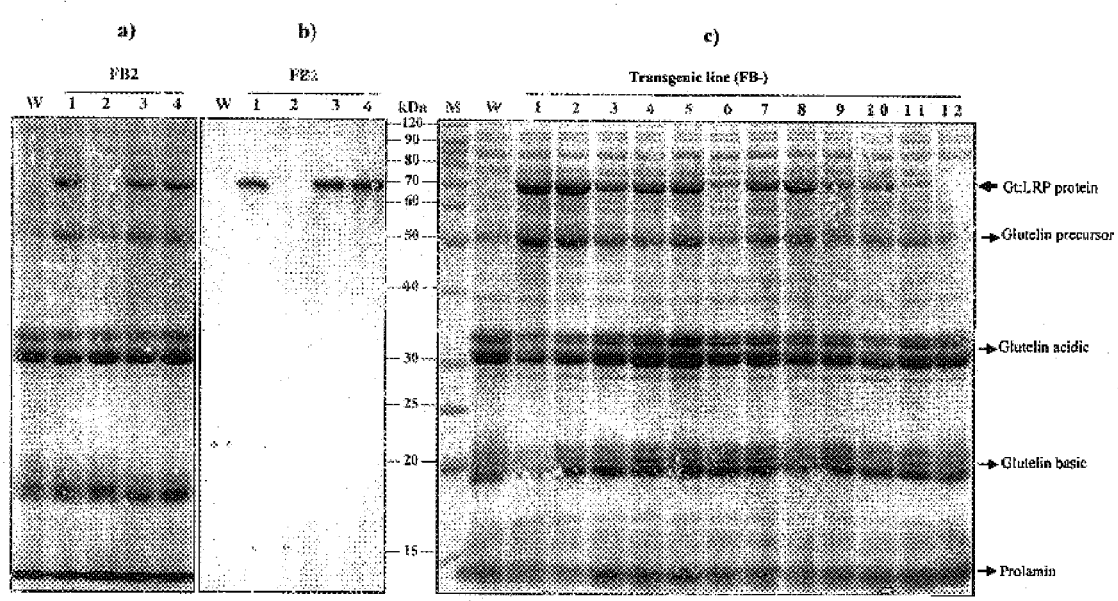
FIGS. 3*a*-3*c* show SDS-PAGE analysis of Gt:LRP fusion protein accumulation in mature seeds of transgenic rice.

The present invention provides methods to obtain production of desired proteins in plants by expressing coding sequences that comprise an amino acid sequence derived from at least one subunit of glutelin and the amino acid sequence of a desired protein. The desired protein may be any protein whose production is desirable, including proteins that may be used for therapeutic purposes or that may be used to enhance the physiology or metabolism of organisms such as mammals, birds and fish. Such proteins include, for example, human growth hormone, human serum albumin, human epidermal growth factor, trout growth factor, human α-interferon, hirudin, erythropoietin, human $\alpha_1$-antitrypsin, human placental alkaline phosphatase, interleukins, human muscarinic cholinergic receptors, glucocerebrosidase, subunit vaccines (e.g., hepatitis B), antibodies, plant oral vaccines and the like. This list is not intended to be exhaustive, but illustrative only.

In one particularly important embodiment, the present invention provides a method to dramatically enhance the nutritional value of the plant parts, including seeds such as rice grains by the introduction and expression of one or more of the invention transgenes. This improvement is not accomplished by increasing the amount of total protein, but by increasing the level of essential amino acid(s). As overabundance of total protein in plant parts would lead to deleterious effects on the texture and storage properties, it is preferable to improve the nutritional quality without alteration in total protein content. The invention method described below is directed to the genetic engineering of natural plant storage protein genes in the way that the recombinant proteins of high nutritional value will be over accumulated in plant parts that can be used for human and animal consumption.

In some embodiments, the desired protein that is produced in plants by virtue of its fusion to a glutelin, has an enhanced value of one or more of the nine essential amino acids. These "essential" amino acids are histidine, isoleucine, leucine, lysine, methionine, phenylalanine, threonine, tryptophan and valine. By "enhanced content" or "enriched" is meant that when the fusion protein is produced in a particular plant, the content of that amino acid is higher than the content of the corresponding amino acid in the unmodified plant. Alternatively, the content of the amino acid in the desired protein is higher than the content of the corresponding amino acid in any protein found in significant levels in the plant. By "significant levels" is meant that the protein constitutes at least 10%, 20%, 30% or even 50% of the total protein content.

As mentioned in the background, rice is relatively unbalanced in amino acid content, with lysine being the first limiting essential amino acid. This is the case for other cereals as well. Thus, an important class of plants subject to the invention is that of the cereals, such as rice, wheat, oats and barley. Taking advantage of the relatively higher efficiency of expression and package system of natural seed storage protein, the present invention provides a method for significant enhancement of the nutritional quality of plant seeds such as cereals by quantitatively modifying the composition of seed proteins. In the examples below, the nutritional quality in transgenic rice seeds was enhanced by increasing the lysine content through fusing the glutelin with LRP. Such increase in lysine content is from two contributors, one is the high lysine content of the LRP polypeptide, and the other is the relatively high level of lysine residues in rice glutelin. The combination of these two lysine contents of glutelin and LRP and the subsequent over accumulation of the Gt:LRP fusion protein in rice endosperm lead to dramatic increase in the essential amino acid lysine.

In one of the embodiments, the seed storage protein gene, rice glutelin Gt1gene, was modified to enrich with lysine residues by fusing with a heterologous cDNA encoding a LRP from winged bean. The fusion gene was transformed to a host cell, preferably a rice cell. The host cell was regenerated into a plant for target protein expression, and progeny obtained. The engineered fusion protein was demonstrated to be seed-specifically expressed and accumulated up to approximately 30% of the total seed protein, and as 2.7% of the seed dry weight, in a high expression transgenic rice line. The over accumulation of fusion protein in seeds resulted in a dramatic increase in the total seed lysine content, amounting to more than 45% over that of the non-transgenic parental line, whereas no statistically significant increase in the total nitrogen of the transgenic seeds was found. Differences in the concentration of some other amino acids in the transgenic seeds were also observed but the rest of the essential amino acids were not significantly decreased (e.g., Met). The high expression of Gt:LRP fusion protein in the transgenic rice seeds appears to have an effect on the expression of other seed proteins and the seed appearance. Several homozygous transgenic lines had been selected from the subsequent progeny of the transformants and field trials were performed. There were no or limited differences in the agronomic performance between the transgenic and control lines. In the feeding trials with growing rats, the transgenic rice seeds gave statistically significant increases in the body weight gain, feed efficiency, true protein digestibility, biological value, and net protein utilization, when compared with the non-transgenic wild-type seeds. These findings demonstrate the feasibility of using genetic engineering to enhance the nutritive value of cereal crops for human and animal consumption.

The foregoing summary describes work that is merely illustrative of the invention. Similar manipulations are well within the skill of the art with respect to alternative desired proteins other than LRP, with respect to a variety of glutelin genes, and with respect to a wide variety of plants.

The invention employs the subunits of glutelins as fusion partners for desired proteins. Glutelins, as seed storage proteins, may be described generally as follows:

Seed storage proteins, such as those from rice, according to their solubility, are classified into albumins (water soluble), globulins (saline soluble), prolamins (alcohol soluble) and glutelins (residue). They are packaged and stored in organelle called protein bodies (PB). Glutelins and globulins are in a vacuolar compartment (PB II), whereas prolamins in endoplasmic reticulum (ER)-derived PB I (Tanaka, K., et al., *Agric. Biol. Chem.* (1980) 44:1633-1639), Okita, T. W., et al., *Annu. Rev. Plant Physiol. Mol. Biol.* (1996) 47:327-350). Glutelin is the major storage protein of rice, accounting for 60-80% of the seed endosperm protein. Compared with other seed storage proteins, rice glutelin contains more lysine residues and is stored in the PB II. It has been proven to be easily digestible by humans and livestock. These characteristics contribute to the better nutritional quality of glutelin than other cereal storage proteins. Moreover, glutelins are encoded by a multigene family consisting of at least six distinct classes (Takaiwa, F., et al., *Seed Proteins* (1999) 401-425, P. R. Shewry, R. Casey, eds., Kluwer Academic Publishers, Dordrecht, The Netherlands), and most of the glutelin genes are highly expressed and accumulated in the rice endosperm. Thus, glutelin can best serve as the fusion receptor protein for efficient production of target proteins to enhance rice nutritional quality.

A requirement for success is a fusion protein structure that can lead to its high level of synthesis and accumulation, which in turn results in significant enhancement in the essential amino acid concerned. Insertion of a desired protein into one or both subunits of the glutelin protein can fulfill this requirement.

The invention includes a method for altering a plant so that it produces seeds or other portions with enhanced nutritional value significantly higher than those not so altered, or so that it produces a protein of interest. The method comprises the steps of:
a) constructing a vector including a DNA construct for expression of a fusion protein as described above;
b) transforming plant cells with the vector utilizing a direct or *Agrobacterium*-mediated transformation system;
c) regenerating a plant cell into a transgenic plant or progeny thereof containing the DNA construct as defined herein; and
d) recovering seeds or other portions such as leaves from the regenerated transgenic plant.

Propagation materials of the transgenic plant or progeny thereof or plant cells are useful in maintaining stock.

The nature of the vector and DNA construct will be dependent on the plant selected for transformation, the manner of transformation, and the portions of the plant in which the desired protein is to be produced. The nature of the promoter influences the portion of the plant where expression occurs; suitable promoters include, for example, the commonly used 35S promoter of cauliflower mosaic virus which is not specific to any particular plant part, as well as those promoters that are more tissue-specific such as the promoters of the maize zein and glutelin genes, and the promoter of the ribulose bisphosphate carboxylase small subunit which is light-inducible, and thus expressible in exposed parts. Other more general genes include housekeeping genes such as the maize actin gene. The patatin gene promoter from potato is particularly suitable as it gives high expression in edible plant parts. Other seed-specific promoters include those associated with those of the multigene family represented by glutelin—e.g., GluA 1-4, GluB 1-4, GluA 2-Gt1 and the like. Other seed-specific genes whose promoters are useful are the prolamin genes (RP3, prol 17, RP5); albumin genes (RA5, 14, 16 and 17); and globulin genes (26 kD and Gb1). The promoter can be selected to provide expression as desired, varying the strength of expression according to the temporal and spatial conditions.

Thus, the expression systems for the fusions of the desired protein are prepared according to known techniques for plant cell expression and the control sequences selected according to the portion of the plant where expression is desired. In most instances, edible portions of the plant will be preferred.

The transformation of plant cells with the vectors thus constructed can be performed by various methods known in the art, including direct DNA uptake, in some cases into protoplasts, or particle bombardment or by the use of microinjection, or by direct incubation of DNA with germinating pollen or employing a plant virus. A commonly used method is *Agrobacterium*-mediated gene transfer which requires the use of vectors that contain DNA segments that integrate into the plant genomic DNA. Thus, the tumor-inducing (Ti) plasmids of *A. tumefaciens* are employed in the vector as these contain transforming DNA which is integrated into the plant cell genome. To construct such vectors, the DNA encoding the fusion protein is flanked by T-DNA border sequences. Selectable markers may also be included in the vectors. This system is particularly useful in dicots, but its use in monocots is also known.

Alternatively, protoplasts may be exposed to a strong electric field in order to effect DNA transfer, or the DNA may be injected using small micropipettes or adsorbed onto microprojectiles such as magnesium sulfate crystals or gold particles.

The resulting cells are selected, if desired, and cultured and then regenerated into plants. The portions containing the fusion protein are then harvested and processed according to the nature of the desired protein.

As noted above, the fusion protein may include a linker which permits recovery of the desired protein portion absent the glutelin fusion. Such cleavage sites may include those susceptible to treatment with enzymes, such as enterokinase or other endopeptidases as well as sites which confer susceptibility to specific cleavage by reagents.

Suitable plants useful in the method of the invention include cereals such as corn, maize, rice, barley, oats, and the like, as well as tuber-forming plants such as yams and potatoes, and any plant that is conveniently grown and contains edible portions.

If the desired protein is a therapeutic or a vaccine, or a diagnostic such as an antibody, recovery of these proteins from the fusion is desirable. They are then used in ways known in the art specific for the particular desired protein produced. If the desired protein is included for the purpose of enhancing the nutritional value of the plant, recovery of the protein from the fusion is still possible, but certainly not necessary. The edible parts of the plants may indeed be used directly as foodstuffs either for human consumption or as animal feed. Standard methods of processing the relevant plant parts for consumption by livestock or as ingredients in recipes intended for humans are as varied as the particular plant and parts chosen and are well known to ordinary practitioners.

OVERVIEW OF THE EXAMPLES

In the examples below LRP is produced at a high level in transgenic rice seeds by making use of the rice native seed storage protein glutelin in fusion with said LRP.

Commercial rice varieties or breeding lines were adopted for our transformation experiments. Procedures for rice tissue culture and *Agrobacterium*-mediated transformation were described previously (Liu, Q. Q., et al., *Acta Phytophysiol Sin* (1998) 24:259-271). Stably transformed plants were regenerated after screening for hygromycin resistance, and $T_0$ transgenic plants were transferred into soil for molecular identification and grown to setting $T_1$ seeds in the greenhouse. $T_2$ seeds harvested from individual $T_1$ plants were used to identify plants with homozygous transgene. Selected homozygous transgenic lines and non-transgenic wild type strain were further propagated for field trial and animal feeding study.

RNA gel blot was conducted to confirm the expression of the fusion gene in transgenic rice grains. Total RNA was isolated from developing rice seeds at 12-15 days after pollination (DAP) by a cold-phenol method (Liu, Q. Q., et al., *Transgenic Res.* (2003) 12:71-82). The blots were hybridized with digoxigenin (DIG)-labeled LRP or Gt1 cDNA fragment, and developed by DIG nucleic acid labeling and detection system (Roche).

The extracted proteins from seeds of transgenic plants were analyzed for their nutritional value. Higher levels of lysine were found in the transgenic seeds as compared to wildtype. In addition, specific transgenic plant lines were identified by assessing levels of production of the fusion protein using SDS gel electrophoresis and Western blot.

The selected homozygous transgenic plant lines were propagated in greenhouse to obtain enough seeds for further large-scale field tests. The field trials were carried out to evaluate and assess the morphological characteristics, yield performance, and other grain physiochemical properties of selected transgenic lines in comparison to the untransformed variety under the same environmental conditions. The main agronomic characteristics were carefully investigated during the course of the trial. After seed maturity, rice grains from individual subplots were harvested and a small portion was used to perform quality evaluation. The remaining seeds were reserved for further propagation and animal feeding tests. All the field trials and further commercial release of the transgenic rice require authorization of the Ministry of Agriculture, China. These were done following the required biosafety guidelines set by the Chinese Government.

The plant seeds generated through the application of the current invention could be used as a novel nutrition-enhanced animal feed or feed supplement. With this aim, the mature seeds of transgenic plant, developed according to the above embodiments using rice as an example, could be non-processed, or dehulled and polished to brown rice, milled rice, and rice bran fraction. The whole grains or one of the processed fractions could be directly used or combined with other ingredients to feed the animals. Animals fed with transgenic rice seeds as their sole or partial dietary source showed significantly higher body weight gain than that of the non-transgenic control group. This shows that notable increases in feed and protein efficiency of transgenic plant seeds were achieved in comparison with those of non-transgenic seeds.

The present invention is not limited to the below disclosed examples. The transgenic seed proteins may be modified and enriched for other desirable nutritional traits for animal and human consumption and applied on other agricultural uses. The following detailed embodiments are offered by way of illustration and should not be interpreted as limitation on the scope of the invention. It will be understood that modifications and variations of what were described here are within the spirit and scope of this patent.

Example 1

Designing Glutelin:LRP Fusion Protein

In this example, two sites in the coding region of acidic and basic subunit of glutelin, respectively, were chosen for insertion of the LRP cDNA, and three categories of chimeric fusion protein genes, Gt:LRP(A), Gt:LRP(B) and Gt:LRP (AB), were developed, representing the insertion of the LRP cDNA into the glutelin coding sequence, in frame, at the acidic subunit (A), at $Ax\downarrow Ay$, the basic subunit (B), at $Az\downarrow Aw$, or both subunits (AB), respectively. The lysine content in the three fusion proteins amount to 4.41 mol %, 4.41 mol % or 5.64 mol %, which is 84%, 84% or 135% higher than that in the regular glutelin, respectively. The three fusion gene constructs were then introduced into rice and their expression and effects on the lysine content of transgenic seeds were studied.

Further work was performed with the Gt:LRP(B) construct. The genomic DNA fragment containing the entire open reading frame of rice glutelin Gt1 gene (Okita, T. W., et al., *J Biol. Chem.* (1989) 264:12573-12581) was cloned and amplified by the addition of BamHI and SacI restriction enzyme sites to the 5' and 3' end, respectively. FIG. 1a shows rice Gt1gene as a 3.8 kb fragment containing all 4 exons, 3 introns, the promoter (1.8 kb) and partial 3' UTR region (136 bp) sequences. Abbreviations of restriction enzyme sites: H, HindIII; B, BamHI; Nc, NcoI; $H_2$, HincII; Sa, SacI; E, EcoRI. The hygromycin phosphotransferase (hpt) gene is the selective antibiotic resistance gene used for rice transformation. The 474-bp cDNA sequence coding the lysine-rich protein (LRP) from winged bean (U.S. Pat. No. 6,184,437, incorporated herein by reference), containing the start codon ATG but not the stop codon, was then inserted into the basic subunit coding region at $Az\downarrow Aw$ of the Gt1 gene, i.e., between the $69^{th}$ and $70^{th}$ nucleotides downstream from the 5' end of the $4^{th}$ Gt1 exon. This does not affect the open reading frame of either rice Gt1 gene or winged bean LRP cDNA, resulting in a fusion gene encoding the Gt:LRP fusion protein with enhanced lysine content. The fusion gene was cloned between the 1.8 kb Gt1 promoter and nopaline synthase (NOS) terminator in the polylinker of binary vector pCAMBIA1300 (web address cambia.com). All of the cloned and fused sequences were confirmed by automatic sequencing, and the resulting plasmid pGLF-B was mobilized into *Agrobacterium tumefaciens* strain EHA105.

9

Example 2

Production of Transgenic Rice

Using a highly efficient *Agrobacterium*-mediated transformation system (Liu, supra, 1998), an elite rice cultivar, Wuxiangjing 9, was transformed with the pGLF-B construct of Example 1. More than 100 primary transgenic rice plants ($T_0$ plants), representing at least 16 independent transgenic lines, FB1-16, were generated after selection on medium containing 50 mg/l hygromycin. Integration of the transgenes into the genome of transgenic plants was further confirmed by DNA gel blot analysis. One to three integrated copies of transgene were found.

FIG. 1*b* shows Southern blots of the transgenic rice plants. Total genomic DNA's (10 μg) from selected primary transformants (lanes 1-12) and non-transgenic plant (lane W) were digested with EcoRI, and hybridized with DIG-labeled LRP cDNA probe (Probe 1 located in FIG. 1*a*). The position of DNA molecular mass markers is indicated. As shown, these extracts could be detected with the probe designed to hybridize to the LRP encoding sequence.

In the greenhouse, most of the transgenic plants exhibited normal phenotype, and set mature seeds for further analysis and propagation. The segregation of transgene among the $T_1$ generation was tested both by PCR analysis and by resistance to hygromycin. The ratio of transgene-positive to -negative seedlings was approximately 3:1 for most transgenic lines (data not shown), indicating the occurrence of a simple transgene locus integration event in the transgenic lines analyzed. After such segregation analysis in $T_1$ and $T_2$ plants, the $T_2$ lines containing the homozygous transgene from each primary transformant were screened.

Example 3

Expression of Fusion Protein Gene in Transgenic Rice Seeds

To assess the expression of the introduced fusion protein gene, the transcription of the fusion protein gene was first tested using total RNA isolated from developing seeds of five primary transgenic rice plants.

As shown in FIG. 2, total RNA (5 μg) from 12-15 DAP developing seeds each of five transformants (lanes FB1, 2, 5, 6 and 8) and non-transgenic rice (lane W) were electrophoresed, blotted onto Nylon membrane, and hybridized with DIG-labeled LRP cDNA (panel a) or Gt1 gene (panel b). Ethidium bromide stained ribosomal RNA under UV light was used to evaluate equal RNA sample for gel loading (panel c).

This analysis showed that only one steady-state transcript was detected in transgenic lines when hybridized with LRP cDNA probe, and the molecular mass of the transcript was as expected. No such transcript was detected in the "W" control rice cultivar (panel a). When hybridizing the same gel with rice Gt1 probe, two types of transcript were displayed in all selected transgenic lines (panel b). The one of low molecular weight, which was also presented in non-transformed plants, represents the native rice glutelin gene transcript; while the other with higher molecular weight and detected only in transgenic lines, represents transcript of the fusion protein gene.

The Northern blot analysis shows that the introduced fusion protein gene was transcribed normally and also shows that the amount of transcript differed among different independent transgenic lines. This was not correlated with the copy number of transgene, and is likely due to the position effect of the transgene. The steady-state level of fusion protein gene transcribed in all transgenic rice lines was lower than that of the native glutelin transcript (panel b).

Example 4

High Accumulation of Fusion Protein in Mature Seeds of Transgenic Rice

The stable expression and high accumulation of fusion protein in the seeds of transgenic plants could be detected by both Coomassie blue staining after SDS-PAGE separation and by immunoblotting analysis as shown in FIG. 3.

Mature seeds from each plant were milled and ground into powder, and the total seed protein was extracted from 100 mg of rice powder in 1.5 ml of extraction buffer (125 mM Tris-Cl, pH 6.8, 4 M urea, 4% SDS and 5% 2-mercaptoethanol) (Yamagata, H., et al., *Plant Physiol.* (1982) 70:1094-1100). The crude extract was centrifuged and the supernatant was used for SDS-PAGE and subsequent Western blot analysis. For quantitation of the expressed fusion proteins in transgenic rice seeds, the standard protein bovine serum albumin (BSA) and the rice total seed protein extract were simultaneously loaded onto the same gel. After electrophoresis, the proteins were stained and scanned into the computer of the GS 690 Imaging Densitometer scan (BioRad) for analysis by the Molecular Analyst® software. For Western blot analysis, protein in the gel was electrophoretically transferred to a nitrocellulose membrane and probed with a rabbit anti-LRP serum. A goat anti-rabbit IgG conjugated to alkaline phosphatase was used to detect the Gt:LRP fusion protein.

Total seed protein was extracted from individual kernels of primary transformant FB2 (lanes 1 to 4) and wild type control (lane W), and subjected to analysis on 10% SDS-PAGE. Coomassie blue staining (panel a), and Western blot analysis using LRP antibody (panel b) show the presence of Gt:LRP in kernels in lanes 1, 3 and 4. Coomassie blue staining analysis of total seed proteins extracted from different independent transgenic FB lines containing homozygous transgene (lanes 1 to 12) and wild type control (lane W) after separation on SDS-PAGE is shown in panel c. (The expressed Gt:LRP fusion protein and rice major storage proteins were indicated by arrowheads on right.) Molecular markers are shown between panels b and c.

In transgenic line FB2, for example, a strong additional band, with a size of about 70 kDa coincided with the estimated size of fusion protein, was clearly visible in ¾ of the $T_1$ mature seeds. This was confirmed to be the fusion protein by immunoblotting with LRP antibody (panels a and b). Out of 12 primary transgenic lines analyzed, 11 lines showed results similar to FB2. Only one line (FB12) did not show fusion protein expression in all the $T_1$ seeds tested.

These results show that the fusion protein could be stably translated and accumulated in the seeds of transgenic rice plants, and also confirmed normal segregation of transgene in their offspring.

One $T_2$ homozygous line from each primary transgenic line was further selected to measure the expression level of fusion protein in mature seeds. As shown in FIG. 3, panel c, the expression level of fusion protein differed markedly among different transgenic lines, FB1 and FB2 being the highest. The amount of fusion protein in transgenic rice seeds, estimated by scanning analysis of stained proteins in the SDS-PAGE, reached 0.2-2.7% of the endosperm dry weight, and accounted for 30% of the total seed proteins in line FB1, on the basis that total seed protein amounts to 8-10% of the mature dry seeds of the parent rice variety.

In the seeds of regular rice, glutelin is initially synthesized as a 57 kDa precursor preproglutelin and transported into the vacuole where it, in part, is proteolytically processed into acidic and basic subunits. Only one steady-state protein was produced from the expression of fusion protein gene in the transgenic rice seeds, which had a molecular mass of the whole fusion protein, indicating that the pre-pro-fusion-protein was not processed in the endosperm of transgenic rice and the processing site between the acidic and basic subunit of glutelin is preserved in the Gt:LRP fusion protein.

tration of amino acids were determined using ion-exchange chromatography on a Beckman 6300 amino acid analyzer following hydrolysis in 6 N HCl for 24 h at 110° C.

TABLE 1

Amino acid composition and total protein content in mature rice seeds of three homozygous transgenic lines and non-transgenic wild type (% of milled seed dry weight)

| Amino acid | WT | FB2 | FB8 | FB1 |
|---|---|---|---|---|
| Asp | 0.914 ± 0.044 | 1.047 ± 0.017 | 0.970 ± 0.030 | 0.929 ± 0.036 |
| The | 0.323 ± 0.018 | 0.380 ± 0.005 | 0.350 ± 0.015 | 0.330 ± 0.010 |
| Ser | 0.419 ± 0.025 | 0.438 ± 0.020 | 0.436 ± 0.019 | 0.397 ± 0.021 |
| Glu | 1.010 ± 0.097 | 1.003 ± 0.073 | 0.901 ± 0.066 | 0.915 ± 0.048 |
| Pro | 0.450 ± 0.008 | 0.466 ± 0.003 | 0.454 ± 0.006 | 0.424 ± 0.010 |
| Gly | 0.455 ± 0.010 | 0.475 ± 0.007 | 0.458 ± 0.024 | 0.446 ± 0.007 |
| Ala | 0.589 ± 0.017 | 0.599 ± 0.010 | 0.592 ± 0.027 | 0.568 ± 0.016 |
| Val | 0.447 ± 0.019 | 0.436 ± 0.019 | 0.457 ± 0.043 | 0.452 ± 0.001 |
| Met | 0.020 ± 0.000 | 0.017 ± 0.002 | 0.020 ± 0.003 | 0.019 ± 0.003 |
| Ile | 0.457 ± 0.015 | 0.509 ± 0.014 | 0.483 ± 0.014 | 0.465 ± 0.019 |
| Leu | 0.844 ± 0.015 | 0.823 ± 0.016 | 0.837 ± 0.059 | 0.821 ± 0.012 |
| Tyr | 0.183 ± 0.036 | 0.154 ± 0.047 | 0.179 ± 0.003 | 0.172 ± 0.025 |
| Phe | 0.543 ± 0.022 | 0.574 ± 0.015 | 0.567 ± 0.016 | 0.535 ± 0.023 |
| His | 0.239 ± 0.006 | 0.253 ± 0.003 | 0.242 ± 0.007 | 0.228 ± 0.008 |
| Arg | 0.756 ± 0.028 | 0.707 ± 0.012 | 0.725 ± 0.023 | 0.677 ± 0.044 |
| Lys | 0.339 ± 0.008 | 0.491 ± 0.012 | 0.385 ± 0.010 | 0.422 ± 0.017 |
| Total protein | 12.63 ± 0.55 | 11.63 ± 0.10 | 12.85 ± 0.12 | 10.92 ± 0.27 |
| Lys (% of protein) | 2.68 ± 0.06 | 4.22 ± 0.10 | 2.99 ± 0.18 | 3.87 ± 0.18 |

*Values represent means of three repeats plus or minus standard errors.

Apart from the additional band of the fusion protein, distinct changes were also observed in the total protein profile of the seeds of several transgenic rice lines, such as FB1, FB2 and FB10, including the reduced expression level of other storage proteins and the lower efficiency of processing the glutelin precursor. The changes in the level of these proteins were further confirmed by the lower levels of their transcripts (data not shown). However, no or little change in the pattern of other storage proteins was also noted in some transgenic lines such as FB5 and FB8 which were accumulating high level of fusion protein (FIG. 3, panel c).

Three homozygous transgenic lines, FB1, FB2 and FB8, which all showed high level of fusion protein, were selected for further evaluation through field, quality and animal feeding trials.

Example 5

Nutritional Composition of Transgenic Rice Seeds

To test the contribution of Gt:LRP fusion protein on the nutritional content of the transgenic rice seeds, homozygous transgenic rice lines and their non-transgenic parent were grown to maturity under the same field conditions. Samples of mature seeds were milled and analyzed for their levels of amino acids and total protein (Table 1). The total protein content in transgenic seeds was comparable with or a little lower than that of the non-transgenic parent. As shown in Table 1, for example, the total crude protein level in mature seeds of the transgenic line FB8 was similar to that of non-transgenic control, whereas the total crude protein levels were lower, by 13.5% and 7.9%, respectively, in the transgenic lines FB1 and FB2. These data show that a decrease in other seed proteins compensates for the high-accumulation of fusion protein in the transgenic seeds.

To analyze the total protein and amino acid composition of the transgenic seeds, the total crude protein content in milled transgenic seeds was calculated from the total nitrogen determined by Kjeldahl method with a factor of 5.95. The concen- As shown in Table 1, consistent with the change in total protein composition, there were noticeable differences in the seed amino acid distribution, especially with respect to lysine. In the dry seeds of transgenic plants with high levels of fusion protein accumulation, the lysine content was significantly increased in comparison with that of the wild type. This increase was positively correlated with the expression level of the fusion protein, and in homozygous transgenic line FB2, could amount to 45% over the control. The lysine content of total protein was also much higher in transgenic seeds than that in the wild-type control, and the increase level, ranging from 10-60% in transgenic lines, was obviously higher than that based on seed dry weight. This enhancement was also accompanied by some changes in concentrations of a few other amino acids, e.g., the contents of aspartic acid, threonine, and isoleucine were significantly increased, while the levels of tyrosine and arginine were somewhat decreased in the transgenic plants. However, the range of changes of these amino acids was much lower than that of lysine.

Therefore, the overall nutritional quality of the rice seed protein, as manifested by the increased content of lysine, was very significantly improved by the expression of the Gt:LRP fusion protein.

Example 6

Field Performance and Grain Quality Evaluation

Field evaluation of the transgenic rice was approved by the Ministry of Agriculture, China in early 2003. Four rice materials, including three homozygous transgenic rice in $T_3$ generation, FB1, FB2, and FB8, and their non-transformed wild type cultivar, Wuxiangjing 9, were used in the trial at the Experimental Farm at Yangzhou University, Jiangsu, China. The rice seeds were sown in a seedling bed for one month and transplanted to a well-isolated safe field. Three replications were arranged for each test material, and in each replication the four test lines were planted as randomized subplots. The size of each subplot was 12.4 m² with 400 plants (a single plant per hill). Standardized normal agronomic practices were followed, and the main agronomic characters were carefully investigated during the course of the experiment. After seed maturity, rice grains from each subplot were individually harvested and their quality evaluation was performed according to the national standards of cereal grain quality of China.

No statistical difference was observed for the morphological characteristics of the whole plant as well as the panicle, among or between different transgenic lines and the untransformed control (Table 2). There were also no distinct differences in the kernel shape (e.g., kernel length and width) and grain physiochemical quality (e.g., starch composition and processing properties) among these rice lines (data not shown). But, a negative effect on the appearance property and weight of grains was observed in the FB2 transgenic line, in which the opaque endosperm phenotype was observed when compared with the untransformed control. As shown in Table 2, the grain chalkiness degree, a factor affecting rice appearance quality, was much higher in the FB2 transgenic line than in the untransformed control. In wild-type control, less than half of the grains showed some chalkiness in their endosperm, and only a little area was opaque within the chalky endosperm. The chalky appearance was observed in almost all of the grains of transgenic line FB2, and the chalky area in each endosperm was enlarged. This was also observed in several other transgenic lines in which the fusion protein was highly expressed and accumulated and the native seed protein profile was altered, such as FB1, FB5 and FB10.

These data show that the negative appearance phenotype is correlated with the high expression of fusion protein and the subsequent change in seed protein profile. The increase in chalkiness degree in the endosperm of FB2 transgenic line led to lighter grain weight, in comparison with the untransformed control, which in turn resulting in a lower yield performance.

However, there are exceptions, as we could still identify and select several transgenic lines, in which the appearance and weight of grains were not affected by their highly expressed fusion protein, as shown by the FB8 line in Table 2. In comparison with the wild-type, transgenic line FB8 did not show any significant difference in its expression profile of native seed proteins, grain components, and yield performance, while the fusion protein was highly expressed and the nutritive value markedly increased in its rice grains.

Example 7

Animal Feeding Trails

Enhancement on the nutritive value of transgenic rice was assessed in feeding trials with growing rats. The grains of each rice line as a mix of the duplications (from three subplots) in the above field trial were well milled, ground, and subsequently used as the only starch and protein source for animal feeding study. The diet ingredients were adopted from the AIN-93G formulation recommended by American Institute of Nutrition (Reeves, P. G., et al., *J. Nutr.* (1993) 123: 1939-1951), which consisted of 850 g/kg milled rice flour, 35 g/kg mineral mix (AIN-93-MX), 10 g/kg vitamin mix (AIN-93G-VX), 40 g/kg fiber, 60 g/kg soybean oil, 3 g/kg cystine, 2.5 g/kg choline bitartrate, and 14 mg/kg tert-butylhydroquinone. For nitrogen balance evaluation, a protein-free diet was prepared by replacement of rice flour and cystine with purified cornstarch.

Four-week-old male Sprague-Dawley rats, with a body weight of 70-80 g, were individually housed in the metabolic cages with stainless steel mesh bottoms, allowing separate collection of feces and urine. Six rats were randomly selected for each diet as a group, and each animal had free access to water and diets during the whole 30 days course of experiment. The intake of diet and gain of body weight by each rat were carefully recorded.

TABLE 2

Agronomy traits and grain chalkiness of transgenic and non-transgenic rice lines from field trial (Yangzhou, China, 2003)

| Rice line | Days to heading | Plant height (cm) | Panicle length (cm) | Panicles per plant | Grains per panicle |
|---|---|---|---|---|---|
| WT | 110.3 (0.6) | 93.3 (2.2) | 16.6 (0.2) | 10.26 (0.46) | 137.3 (2.9) |
| FB2 | 110.7 (0.6) | 93.7 (1.5) | 17.0 (0.5) | 10.29 (0.02) | 132.5 (9.8) |
| FB8 | 110.7 (0.6) | 92.2 (1.2) | 16.8 (0.7) | 10.35 (1.09) | 135.3 (5.1) |

| Rice line | Seed setting per panicle (%) | 1000-grain weight (g) | Expected yield per plant (g) | Chalkiness Grain number (%) | Area per grain (%) | Degree (No. × area) (%) |
|---|---|---|---|---|---|---|
| WT | 78.8 (4.9) | 24.86 (0.05) | 27.61 | 42.0 | 16.9 | 7.1 |
| FB2 | 80.3 (8.3) | 22.87 (0.09) | 25.04 | 94.0 | 37.8 | 35.5 |
| FB8 | 78.6 (7.4) | 24.73 (0.20) | 27.23 | 56.0 | 14.5 | 8.1 |

Standard errors are shown in parentheses.

As shown in Table 3, rats consumed more transgenic seed-based diets in comparison with the non-transgenic one. In the case of transgenic meals, more than 12 grams were taken in every day by each rat, as compared to 9.5 grams in the non-transgenic diet. Statistically significant increases were observed in the true protein digestibility, biological value, and net protein utilization of the transgenic diets. Rats receiving transgenic rice seeds as their sole nitrogen source gained significantly higher body weight than did the non-transgenic control group.

TABLE 3

Nutritional evaluation of transgenic and non-transgenic rice by rat feeding

| Rice | Body weight gain (BWG) (g/d/rat) | Diet intake (DI) (g/d/rat) | Feed efficiency (g BWG/g DI) | Protein efficiency (g BWG/g Protein intake) | True protein digestibility (% of N intake) | Biological value (% of absorbed N) | Net protein utilization (% of N intake) |
|---|---|---|---|---|---|---|---|
| WT | 1.07 (0.13) | 9.50 (0.83) | 0.113 (0.013) | 1.25 (0.15) | 94.34 (1.17) | 89.82 (2.63) | 84.73 (2.21) |
| FB2 | 2.19 (0.21) | 12.21 (0.86) | 0.179 (0.012) | 2.04 (0.13) | 96.81 (0.87) | 94.11 (1.16) | 91.10 (0.99) |
| FB8 | 2.16 (0.24) | 12.90 (0.87) | 0.168 (0.011) | 1.80 (0.12) | 97.05 (0.46) | 92.58 (2.99) | 90.01 (3.05) |
| FB1 | 1.95 (0.29) | 11.87 (1.16) | 0.164 (0.011) | 2.00 (0.13) | 97.27 (0.67) | 94.03 (2.12) | 91.46 (2.26) |

Standard errors are shown in parentheses.

The invention claimed is:

1. An expression system operable in plant cells which comprises a nucleotide sequence encoding a fusion protein which comprises the amino acid sequence of at least one acidic or basic rice glutelin subunit and the amino acid sequence of a desired protein operably linked to control sequences that effect its expression in plant cells.

2. The expression system of claim 1 wherein the desired protein is lysine-rich protein from *P. tetragonolobus* (LRP).

3. The expression system of claim 1 wherein the fusion protein further comprises a linking sequence comprising a cleavage site between the glutelin subunit and the desired protein.

4. A vector comprising the expression system of claim 1.

5. The vector of claim 4 which is included in *Agrobacterium*.

6. Plant cells modified to contain the expression system of claim 1.

7. Plant cells of claim 6 which are cereal plant cells.

8. A plant or plant part which comprises the cells of claim 6.

9. The plant part of claim 8 which is a seed.

* * * * *